US006500973B2

(12) United States Patent
Fontenot (10) Patent No.: US 6,500,973 B2
(45) Date of Patent: Dec. 31, 2002

(54) EXTRACTIVE SOLUTION CRYSTALLIZATION OF CHEMICAL COMPOUNDS

(75) Inventor: Kevin J. Fontenot, Kingsport, TN (US)

(73) Assignee: Eastman Chemical Company, Kingsport, TN (US)

(*) Notice: Subject to any disclaimer, the term of this patent is extended or adjusted under 35 U.S.C. 154(b) by 26 days.

(21) Appl. No.: 09/870,988

(22) Filed: Jun. 1, 2001

(65) Prior Publication Data
US 2002/0035284 A1 Mar. 21, 2002

Related U.S. Application Data
(60) Provisional application No. 60/208,565, filed on Jun. 2, 2000.

(51) Int. Cl.$^7$ .............................. C07C 231/24
(52) U.S. Cl. ..................... 554/70; 554/68; 554/47
(58) Field of Search ................. 554/47, 68, 70

(56) References Cited

U.S. PATENT DOCUMENTS

| | | | |
|---|---|---|---|
| 2,398,526 A | 4/1946 | Greenburg | 260/674 |
| 2,520,716 A | 8/1950 | Fetterly | 260/676 |
| 2,768,222 A | 10/1956 | Nixon et al. | 260/674 |
| 2,778,864 A | 1/1957 | Fenske | 260/674 |
| 2,941,019 A | 6/1960 | Foreman et al. | 260/674 |
| 3,767,724 A | 10/1973 | Gouw | 260/676 |
| 4,107,443 A | 8/1978 | Mark et al. | 568/750 |
| 4,371,470 A | 2/1983 | Matsukura et al. | 260/428 |
| 4,634,551 A | 1/1987 | Burns et al. | 252/102 |
| 4,681,695 A | 7/1987 | Divo | 252/94 |
| 4,852,989 A | 8/1989 | Burns et al. | 8/107 |
| 4,980,463 A | 12/1990 | Walkup et al. | 536/124 |
| 5,298,611 A | 3/1994 | Navia et al. | 536/4.1 |
| 5,391,780 A | 2/1995 | Zima et al. | 554/69 |
| 5,391,783 A | 2/1995 | Colignon et al. | 554/98 |
| 5,393,901 A | 2/1995 | Zima et al. | 554/69 |
| 5,393,905 A | 2/1995 | Zima et al. | 554/70 |

(List continued on next page.)

FOREIGN PATENT DOCUMENTS

| | | |
|---|---|---|
| DD | 295 349 A5 | 10/1991 |
| EP | 0 402 339 A1 | 12/1990 |

(List continued on next page.)

OTHER PUBLICATIONS

Chivate et al., "Separation of m–cresol and p–cresol by extractive crystallization", *Chemical Engineering Sience*, vol. 5, pp. 282–241, (1956).

(List continued on next page.)

*Primary Examiner*—Deborah D. Carr
(74) *Attorney, Agent, or Firm*—Bernard J. Graves; Michael J. Blake (57) ABSTRACT

A process for the purification and isolation of a chemical compound, by extractive solution crystallization. The process comprises combining in any order a first solvent, a second solvent, and a mixture comprising a chemical compound with at least one impurity. The second solvent phase extracts impurities out of the first solvent, and keeps the impurities dissolved to avoid their co-crystallization with the phenyl ester salt. Once the chemical compound has crystallized out of solution, it is collected, washed and/or dried. The second solvent may be added after the mixture containing at least one chemical compound is dissolved in a first solvent, as long as the second solvent phase is added prior to the end of crystallization. Advantageously, this invention combines the previously distinct steps of extraction and crystallization in one unit operation. The process may be used with a variety of chemical compounds particularly, phenyl ester salts, including but not limited to sodium 4-sulfophenyl-6-[(1-oxynonyl)amino] hexanoate, sodium 4-(nonanoyloxy) benzenesulfonate, and sodium benzoyloxybenzenesulphonate.

25 Claims, 3 Drawing Sheets

U.S. PATENT DOCUMENTS

| | | | |
|---|---|---|---|
| 5,414,099 A | 5/1995 | Heinzman et al. | 554/69 |
| 5,429,773 A | 7/1995 | Sherry et al. | 252/554 |
| 5,466,840 A | 11/1995 | Lutz et al. | 554/70 |
| 5,523,434 A | 6/1996 | Burns et al. | 554/68 |
| 5,534,195 A | 7/1996 | Chapman et al. | 510/444 |
| 5,534,196 A | 7/1996 | Chapman et al. | 252/186.27 |
| 5,650,527 A | 7/1997 | Lutz et al. | 554/68 |
| 5,717,118 A | 2/1998 | Lutz et al. | 554/69 |

FOREIGN PATENT DOCUMENTS

| | | | | |
|---|---|---|---|---|
| EP | 415 472 A1 | 3/1991 | | |
| EP | 0 484 634 A1 | 5/1992 | | |
| GB | 2 249 104 A | 4/1992 | | |
| JP | 6-179648 | 6/1994 | | |
| JP | 6-306042 | 11/1994 | | |
| JP | 8-245549 | 9/1996 | | |
| JP | 9-110824 | 4/1997 | | |
| JP | 0 911 0 824 | 4/1997 | | C07C/309/42 |
| WO | WO 94/18159 | 8/1994 | | |
| WO | WO 94/28104 | 12/1994 | | |
| WO | WO 94/281061 | 12/1994 | | C11D/3/39 |
| WO | WO 95/07883 | 3/1995 | | |
| WO | WO 96/16148 | 5/1996 | | |
| WO | WO 97/27280 | 7/1997 | | |
| WO | 99/09004 | * 2/1999 | | |
| WO | WO 99/09004 | 2/1999 | | |

OTHER PUBLICATIONS

Dikshit et al., "Separation of Organic Isomers by Extractive Crystallisation", *Indian Chemical Journal*, pp. 24–29, Jan. 1969.

Dikshit et al., "Separation of ortho and para nitrochlorobenzenes by extractive crystallisation", *Chemical Engineering Science*, vol. 25, pp. 311–317, (1970).

Dikshit et al., "Selectivity of solvent for extractive crystallisation", *Chemical Engineering Science*, vol. 26, pp. 719–727, (1971).

Dye et al., "Bypassing Eutectics with Extractive Crystallization: Design Alternatives and Tradeoffs", *Process Systems Engineering*, vol. 41, No. 6, pp. 1456–1470, Jun. 1995.

Egan et al., "Separation of Xylenes Selective Solid Compound Formation with Carbon Tetrachloride", *Industrial and Engineering Chemistry*, vol. 47, No. 2, pp. 250–253. 1995.

Findlay et al., "Separation and Purification By Crystallization", pp. 130–131. 1995.

Findlay, "Adductive Crystallization", pp. 257–318. 1981.

Gerhartz, "Crystallization and Precipitation", *Ullmann's Encyclopedia of Industrial Chemistry*, vol. B2, pp. 3-1–3-46, (1988).

Lashanizadegan et al., "Dissociation Extractive Crystallization: Separation of Di– and Trichloroacetic Acids", *Chemical Engineering Research and Design*, vol. 74, Part A, pp. 773–775, Oct. 1996.

Lynn et al., "Recovery of Anhydrous $Na_2SO_4$ from $SO_2$–Scrubbing Liquor by Extractive Crystallization: Liquid–Liquid Equilibria for Aqueous Solutions of Sodium Carbonate, Sulfate, and/or Sulfite Plus Acetone, 2–Propanol, or tert–Butyl Alcohol", *Ind. Eng. Chem. Res.*, vol. 35, pp. 4236–4245, (1996).

McKetta et al., "Crystallization, Extractive and Adductive", *Encyclopedia of Chemical Processing and Design*, vol. 13, pp. 456–506., 1991.

Nagahama et al., "Vapor–liquid–solid equilibria of ternary, liquefied gas–benzene–cyclohexane systems and their application in a new process of crystallization", *International Chemical Engineering*, vol. 31, No. 2, pp. 359–369, Apr. 1991.

Rajagopal et al., "Design and Economic Trade–Offs of Extractive Crystallization Processes", *AIChE Journal*, vol. 37, No. 3, pp. 437–447, Mar. 1991.

Savitt et al., "Separation of m– and p–Cresols from Their Mixtures", *Industrial Engineering Chemistry*, vol. 44, No. 10, pp. 2428–2431, Oct. 1952.

Tare et al., "Separation of Close Boiling Isomers By Adductive and Extractive Crystallization", *AIChE Symposium Series*, vol. 72, No. 153, pp. 95–99, (1976).

Weingaertner et al., "Extractive Crystallization of Salts from Concentrated Aqueous Solution", *Ind. Eng. Chem. Res.*, vol. 30, pp. 490–501, (1991).

Zerres et al., "Thermodynamics of Phase Equilibria in Aqueous–Organic Systems with Salt", *AIChE Journal*, pp. 676–691, vol. 40, No. 4, Apr. 1994).

* cited by examiner

EXTRACTIVE SOLUTION CRYSTALLIZATION OF CHEMICAL COMPOUNDS

This application claims priority under 35 U.S.C. § 119 to provisional application Ser. No. 60/208,565, filed Jun. 2, 2000, which is incorporated herein by reference.

FIELD OF THE INVENTION

This invention relates to extractive solution crystallization techniques for a broad class of chemical compounds, including salts of chemical compounds. More particularly, the invention relates to a process for the isolation and purification of inorganic salts or organic salts by extractive solution crystallization. In a highly preferred embodiment, the invention relates to phenyl ester salts.

BACKGROUND OF THE INVENTION

Phenyl ester salts, as are known in the art, have been used in detergents and as bleach activators for fabric laundering and cleaning applications. The synthesis and purification of phenyl ester salts is described in U.S. Pat. No. 5,717,188, U.S. Pat. No. 5,650,527, and U.S. Pat. No. 5,523,434. In most cases, the phenyl ester salt to be purified is first isolated in a crude form, for example, through either evaporation of the reaction solvent, or by solid-liquid separation through filtration or centrifugation. This crude product is then purified using techniques known in the art, such as distillation or crystallization.

For the isolation and purification of solid chemical compounds, crystallization is often more appropriate than distillation. Crystallization comprises precipitating a chemical compound from a solution, followed by crystal growth. As a purification technique, crystallization has been used extensively to separate inorganic and organic chemical compounds from impurities, and thereby purifying the inorganic or organic chemical compound.

Many industrial chemical processes isolate and purify chemical compounds using crystallization techniques. Comprehensive accounts of various crystallization techniques have been discussed in several publications. (See Mullins, J. W., "Ullmann's Encyclopedia of Industrial Chemistry," Volume B2, 3-1, 1988, for example). In many situations, crystallization can yield compounds of high purity in one theoretical stage with minimal energy costs. In other cases, however, crystallization may be inefficient for a variety of reasons.

One problem commonly encountered when using crystallization techniques is the co-crystallization of undesired impurities. These impurities may include, for example, unreacted starting materials or undesired byproducts produced during synthesis. In the case of phenyl ester salts, co-crystallization can lead to purity or separability problems which preclude isolation of the phenyl ester salt or which preclude its intended use in a subsequent chemical process or product. The impurities can sometimes be removed through multiple purification or recrystallization steps. However, the use of numerous purification or recrystallization steps has many disadvantages including: high capital costs, low overall yield, loss of product, poor product quality, lack of process robustness, additional steps for solvent recovery, and slower throughput. For large scale production, these problems can be particularly unacceptable.

Generally, simple fractional crystallization is used to separate and/or purify chemical compounds from crude mixtures containing the desired compound and one or more undesired impurities. Simple fractional crystallization is the sequential and separate crystallization of more than one compound from the same solution. Where simple fractional crystallization cannot be used to completely separate pure chemical compounds from mixtures, crystallization techniques such as adductive crystallization and extractive crystallization have been employed. Adductive crystallization processes have been described, for example, in U.S. Pat. Nos. 2,768,222; 2,778,864; and 2,520,716. Extractive crystallization processes have been described, for example, in U.S. Pat. Nos. 3,767,724 and 2,398,526.

Both adductive crystallization and extractive crystallization have been effectively used to (i) separate mixtures which form eutectics upon crystallization, (ii) separate pure isomers where distillation, extraction, and adsorption fail, (iii) separate compounds by shape and size rather than by chemical type, and (iv) eliminate deep refrigeration (e.g., Dale, G. H., "Crystallization, Extractive and Adductive," in Encyclopedia of Chemical Processing and Design, J. J. McKetta and W. A. Cunningham, Eds., Vol. 13, p. 456, 1981).

Adductive crystallization involves adding an adductive agent to a solution containing a mixture of chemical compounds to selectively form an adduct with a desired chemical compound, which then selectively crystallizes or crystallizes out of the solution. The resulting adduct may then be separated as a solid from the mixture. The desired product is subsequently recovered by "breaking" the adduct and removing the adductive agent. Disadvantages of adductive crystallization include the extra steps which are required to isolate the desired chemical compound, as well as the mechanical problems and large expense involved if this process is to be adapted for large scale production. Further, some chemical compounds, such as the detergent or bleach activators described below, may not be stable under the conditions required to remove the adductive agent from the resulting adduct of the compound.

Extractive crystallization, in contrast, involves adding an additional component, such as a solvent, to a solution containing a mixture of chemical compounds (e.g., isomers, binary pairs, or similar compounds) to lower the eutectic point of the mixture. Extractive crystallization affords enhanced recovery of the purified desired component as a solid, and may also allow the recovery of the other isomer as a purified co-product. Extractive crystallization is normally limited to separations of fairly high molecular weight compounds with relatively high freezing points (Dale, G. H., "Crystallization, Extractive and Adductive," Encyclopedia of Chemical Processing and Design, J. J. McKetta and W. A. Cunningham, Eds., Vol. 13, p. 456, 1981; Dye, S. R. et al, Process Systems Engineering, 41, 1456–1470, 1995). Methods for selecting the extractive solvent for extractive crystallization have been studied (e.g., Dikshit, et al., Chem. Eng., Science, 26, 719–727, 1971). However, extractive crystallization is not readily adaptable to a wide variety of substrates or solvent systems.

Extractive crystallization has also been adapted to crystallize salts from concentrated aqueous solutions. Here, the added solvent extracts the water away from the inorganic salt phase (e.g., Weingaertner, D. L., et al., Ind. Eng. Chem. Res., 30, 490–501, 1991; Zerres, H., et al., A. I. Ch. E., 40, 676–691, 1994; Lynn Scott, A. L., et al., Ind. Eng. Chem. Res., 35, 4236–4245, 1996). This results in the crystallization and crystal growth of the salt solute, as the original aqueous phase becomes more concentrated and its saturation limit is exceeded. This mechanism is different from conventional extractive crystallizations since two liquid phases are actually present. However, both of these phases are considered to be aqueous, and not biphasic.

Another recent offshoot of extractive and adductive crystallization techniques is dissociation extractive crystallization (Lashanizadegan, A. et al., *Chem. Eng. Res. and Design, Trans. Inst. Chem. Eng.*, 74, Part A, 1996). Here, the extractant contains a reactive agent that reacts with the desired compound in either the same phase or a separate phase. The resulting product or complex is insoluble and crystallizes out. Since the reaction is equilibrium-based, an excess of the extractant that contains the reactive agent may be used to recover the desired compound in high yields. As with adductive crystallization, however, further processing steps are required to ultimately isolate the desired product from the complex. Often, the desired product must be recovered from the complex through additional steps, such as heating or other chemical means. Similar problems as described above for adductive crystallization are encountered, which limits the utility of this technique.

Extractive crystallization using biphasic systems is described in U.S. Pat. No. 5,298,611 and U.S. Pat. No. 4,980,463. These patents are generally limited to sucralose esters, and have not been generally adapted to the purification of salts of chemical compounds or phenyl ester salts. U.S. Pat. No. 5,298,611 patent teaches using a biphasic mixture (in a ratio of 4:1 to 1:2 water to organic) for crystallization. The crystallization appears to be practiced as a "drown-out" crystallization, where the second solvent is added to cause the desired compound of choice to precipitate out, rather than effecting crystallization by cooling or evaporation.

In U.S. Pat. No. 4,980,463 a sucralose pentaester is crystallized in a biphasic mixture. The crystallization of the sucralose pentaester is in the organic phase while the impurities are in the aqueous phase. The ratio of aqueous to organic appears to be between 1:1 and 1:5.

Therefore, in spite of the development of such highly complex crystallization techniques, there still exists a need in the art for a crystallization technique that produces satisfactory results in terms of ease of operation, purity of final product, and efficiency.

Such crystallization techniques are particularly needed with respect to phenyl ester salts, which are used in detergents and cleaning formulations as bleach activators. For instance, numerous solvents have been investigated for the purification of sodium 4-sulfophenyl-6-[(1-oxynonyl)-amino] hexanoate after separation from sulfolane, including acetic acid, water, methanol, isopropanol, and combinations thereof (e.g., U.S. Pat. No. 5,523,434). However, the purification of sodium 4-sulfophenyl-6-[(1-oxynonyl)-amino] hexanoate is not trivial. All the processes developed to purify sodium 4-sulfophenyl-6-[(1-oxynonyl)-amino] hexanoate have been suboptimal for reasons including poor yield, high capital costs, low rate of perhydrolysis, poor product color and lack of process robustness. Also, high capital costs are encountered in cases requiring additional crystallizations, solvent recovery, and/or special equipment for slow filtering or settling solids.

Accordingly, it would be beneficial to have a general crystallization process, (particularly for detergents and bleach activators), which avoids problems of co-crystallization, can be performed over a wide temperature range under mild conditions, and provides the desired product in high yields. The invention described below answers this need.

SUMMARY OF THE INVENTION

The invention relates to a process for the isolation and purification of salts of chemical compounds, such as phenyl ester salts, by extractive solution crystallization. Extractive solution crystallization is the process whereby a salt of an inorganic or organic chemical compound is crystallized from a solvent system comprising a first solvent and a second solvent. In this process, extraction is combined with solution crystallization. The invention is different from conventional extractive crystallization, because it employs systems with two liquid phases, one aqueous, and one organic. Additionally, the invention advantageously does not require the reaction of the desired product to form an adduct, as in adductive crystallization. Extractive solution crystallization may be particularly useful in avoiding situations where an impurity cocrystallizes with the desired product.

The first step of the process involves combining in any order: a first solvent, a second solvent, and a mixture comprising a chemical compound and at least one impurity. The solvents are selected such that the chemical compound is substantially soluble in the first solvent and substantially insoluble in the second solvent. Further, the impurity is substantially soluble in the second solvent. The second solvent is substantially immiscible in the first solvent under conditions where a chemical compound crystallizes from the first solvent. The second solvent may initially be miscible in the first solvent at the dissolution temperature of the system, and then form at least two phases during the course of the crystallization prior to the precipitation of any impurities. It is permissible for the second solvent to form a separate phase during the course of the crystallization, as long as it is present as a second phase prior to the anticipated precipitation of any impurities.

The mixture comprising a chemical compound and at least one impurity is then substantially dissolved in the solvents. The mixture may be dissolved directly in a combination of the first and second solvents. Alternatively, the mixture may be first dissolved in one solvent, followed by the addition of the second solvent, prior to the crystallization step or the precipitation of any impurities. The dissolving step can be achieved through stirring and/or heating, or other methods as will be apparent to one skilled in the art. At the end of the dissolving step, any remaining undissolved material from the above steps may be optionally removed, e.g, by filtration. The chemical compound is crystallized from the first solvent under conditions where the impurity remains substantially dissolved in the second solvent. After crystallization, the crystals are collected.

The invention describes a process that is applicable to a broad range of inorganic and organic chemical compounds as well as salts of inorganic and organic compounds. In a preferred embodiment, the invention is used as a process to purify phenyl ester salts. For clarity, the invention is described with regard to purifying phenyl ester salts. The process of the invention substantially improves the properties of the resulting purified phenyl ester salts. For salts of phenyl esters which are used as detergents or bleach activators such improvements include, but are not limited to, greater purity, larger particle size, and improved product color over other methods of purification. In addition, this invention advantageously combines into one unit operation, the previously separate steps of solid-liquid separation, extraction, drying, and re-crystallization. This reduces capital costs over multi-step processes and results in higher efficiency. In industrial process chemistry, increased throughput on a given device can be the difference between an economic process and an uneconomic process.

A further aspect of this invention is that the impurities that are dissolved in the second solvent may easily be isolated and recycled. These impurities may include unreacted starting material, or other useful side products, for instance. For large-scale production, this may be a highly desirable advantage.

In particular, the invention provides a more efficient process for the separation and purification of sodium 4-sulfophenyl-6-[(1-oxynonyl)-amino] hexanoate without requiring the pre-extraction of water insoluble impurities, or compromising on yield, stability, or purity of product. This invention alleviates problems encountered previously when crystallizing sodium 4-sulfophenyl-6-[(1-oxynonyl)-amino] hexanoate directly from water, including slow filtering and foaming during the filtration step.

Additional objects and advantages of the invention are discussed in the detailed description that follows, and will be obvious from that description, or may be learned by the practice of the invention. It is to be understood that both this summary and the following detailed description are exemplary and explanatory only and are not intended to restrict the invention.

DETAILED DESCRIPTION

The invention relates to extractive solution crystallization, which is a process for the isolation and purification of salts of chemical compounds, including phenyl ester salts, bleach activators and detergents.

As mentioned above, phenyl ester salts are used as bleach activators in laundry detergents and other cleaning formulations. As shown in the reaction scheme below, the phenyl ester salt is hydrolyzed upon nucleophilic attack by a perhydroxide anion to yield a peroxy acid that acts as a bleaching agent and a substituted phenolic anion.

To be effective as a bleach activator, the phenyl ester salt must readily react with a perhydroxide anion to produce (activate) the corresponding peroxyacid within the length of time and at the temperature of a typical wash cycle. Employing the process of the invention improves the perhydrolysis rate of phenyl ester salts. Advantageously, then, this invention improves the efficacy of the detergent containing a phenyl ester salt bleach activator. The process of the invention can be used with any phenyl ester salt.

Exemplary phenyl ester salts, which are used as bleach activators, are described in U.S. Pat. Nos. 4,634,551; 4,852,989; 5,391,780; 5,393,905; 5,393,901; 5,414,099; 5,466,840; 5,523,434; 5,650,527; and 5,717,118; as well as in published PCT applications WO 94/18159, WO 95/07883, WO 96/16148, and WO 99/09004. These U.S. Patents and published PCT applications are incorporated herein in their entirety.

Examples of phenyl ester salts, which may be isolated and purified using the process of this invention, include the compounds described by formula (I) or (II) below:

$R^1$ is selected from $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl. Preferably, $R^1$ is selected from $C_6$–$C_{10}$ alkyl, and $C_6$–$C_{10}$ aryl.

$R^2$ and $R^5$ are each independently selected from hydrogen, $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl. Alternatively, in formula II, $R^2$ and $R^5$, together with the nitrogen carrying them, form a $C_3$–$C_{10}$ heterocycle. This heterocycle may or may not contain additional heteroatoms selected from: nitrogen, oxygen, sulphur, or phosphorous. Preferably, $R^2$ is hydrogen, and $R^5$ is selected from hydrogen, $C_6$–$C_{10}$ alkyl, and $C_6$–$C_{10}$ aryl.

$R^3$ and $R^4$ are each independently selected in each instance from hydrogen, $C_1$–$C_{10}$ alkyl, $C_2$–$C_{10}$ alkenyl, $C_2$–$C_{10}$ alkynyl, $C_3$–$C_{10}$ cycloalkyl, and $C_6$–$C_{10}$ aryl. The $R^3$ and $R^4$ groups, together with the carbon carrying them, may form a $C_3$–$C_{10}$ cycloalkyl group. This cycloalkyl group may or may not contain heteroatoms selected from: nitrogen, oxygen, sulphur, or phosphorous. Preferably, $R^3$ and $R^4$ are independently selected in each instance from hydrogen and methyl.

The substituent Y on the phenyl ring is selected from $SO_3^-M^+$, $CO_2^-M^+$, $SO_4^-M^+$, and $N^+(R^6)_3X^-$. M represents a cation, and may be selected from hydrogen, ammonium and alkali metal atom. $R^6$ in each instance is independently a $C_1$–$C_4$ alkyl group. X is an anion, and may be selected from a halide, hydroxide, methylsulfate, or acetate ion. Preferably, Y is selected from $SO_3^-M^+$, and $CO_2^-M^+$; where M is a sodium ion.

The phenyl ring may also be further substituted with 1 to 4 other substituents. The substituents may be electron-withdrawing or electron-donating groups. The substituents may, for example, be chosen to adjust the perhydrolysis rate, to adjust the hydrophilic/hydrophobic nature of the phenyl ester salt, or to adjust the solubility of the phenyl ester salt. Possible groups include, but are not limited to, hydroxyl, halogen, $C_1$–$C_{10}$ alkyl, $C_2$–$C_{10}$ alkenyl, $C_2$–$C_{10}$ alkynyl, $C_3$–$C_{10}$ cycloalkyl, and $C_1$–$C_{10}$ alkoxy, and amino groups. When the phenyl ester salts are to be used as bleach activators, it is also desirable to have electron-withdrawing groups on the phenyl ring, to facilitate nucleophilic attack by a perhydroxide anion. In general, a substituted phenol is the preferred leaving group, however there may be other acceptable leaving groups, as will be evident to one of ordinary skill in the art. The substituted phenyl group should be sufficiently reactive for the reaction to occur within an optimum time frame, such as a wash cycle. The leaving group should also be sufficiently stable to ensure that the rate of back reaction will be negligible. However, the substituted phenyl group should not be too reactive, as this may lead to storage and stability problems in a bleaching or detergent formulation.

The value of "m" is 0 or 1 and represents the presence or absence of an amido group in the compound. Acceptable values for "n" may range from about 0 to 20, and preferred values for "n" include from about 0 to about 6. When used as a bleach activator, the value of "n" in formulae I or II for the phenyl ester salt may be dictated to a large extent by the hydrophilicity of the resulting phenyl ester salt. The value of "n" and the choice of the various substitutions or solubilizing groups should preferably be selected such that the resulting peroxy acid is water soluble.

The bleaching effectiveness of the resulting peroxy acid resulting from the phenyl ester salt may be related to its hydrophilic/hyprophobic balance. This balance, related to the choice of "m" and particularly "n", affects the solubility of the peroxy acid in water. In addition, the hydrophilic/hydrophobic balance determines which types of stains and soils that the molecule will bleach most efficiently. The presence of an amido group in the phenyl ester salt may impart certain desirable features to a bleach activator, as described in U.S. Pat. No. 4,852,989. For example, in certain circumstances, the presence of an amido group has been found to lower the vapor pressure and/or increase the melting point of the resulting peroxyacid thereby increasing the stability of the peroxyacid. Additionally, it is generally preferred to choose the value of "n" and various substituents to increase the water solubility of the peroxyacid.

For the various substituents of the phenyl ester salts of formula (I) or (II), the alkyl, alkenyl, and alkynyl groups may be straight or branched. The alkyl, alkenyl, and alkynyl groups may be optionally substituted with halogen, alkoxy groups, or water-solubilizing groups. In addition, these groups may also be substituted with various steroids, natural products and fatty acids, as known in the art.

A "water-solubilizing group" is a substituent that increases the solubility of a compound in aqueous solution. Exemplary water-solubilizing groups include, but are not limited to, quaternary amine, sulfate, sulfonate, carboxylate, phosphate, phosphonate, polyether, polyhydroxyl, boronate, and amide groups such as —$CONH_2$ and $CONHCH_3$. The water solubilizing groups may also include sulfo, sulfonamido, carbonamido, sulfamoyl, carbamoyl, hydroxyl, and salts thereof.

The $C_2$–$C_{22}$ alkenyl and $C_3$–$C_{22}$ alkynyl groups represent straight or branched chain hydrocarbon radicals containing 2 to 22 carbons in the chain and which contains at least one of a carbon-carbon double bond and/or at least one of a carbon-carbon triple bond.

The $C_3$–$C_{22}$ cycloalkyl heterocycles and rings may contain more than one degree of unsaturation and may be unsubstituted or substituted. The heterocycles and cycloalkyl rings may be optionally substituted with halogen, alkoxy groups, or water-solubilizing groups. These rings may be monocyclic, bicyclic, or polycyclic. In addition, these cycloalkyl rings may or may not contain one or more heteroatoms in the ring. Acceptable heteroatoms are selected from: oxygen, nitrogen, sulfur and phosphorus.

The $C_6$–$C_{14}$ aryl ring may be monocyclic, bicyclic, or polycyclic. In addition, the aryl ring may contain one or more heteroatoms. Appropriate heteroatoms include oxygen, nitrogen, sulfur, and phosphorus. Both the $C_3$–$C_{22}$ cycloalkyl rings and $C_6$–$C_{14}$ aryl rings may be substituted with appropriate $C_1$–$C_4$ alkylaryl, hydroxy, $C_1$–$C_4$ alkanyloxy, halogen or water-solubilizing groups. The aryl group may be substituted or unsubstituted. The term "aryl" includes carbocyclic aryl groups containing up to fourteen carbons, e.g., phenyl and naphthyl. The term "aryl" also includes heterocyclic aryl groups such as a 5 or 6-membered heterocyclic aromatic ring. These heterocyclic aromatic rings may also contain other heteroatoms selected from: oxygen, nitrogen, sulphur, and phosphorous. These heterocyclic aryl rings may be optionally fused to one or two phenyl rings or another 5 or 6-membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl, and the like. The aryl groups may be substituted or unsubstituted as discussed above for the alkyl, alkenyl, and alkynyl groups.

In addition, the term "aryl" includes arylene groups. The term "arylene" defines a divalent carbocyclic aryl hydrocarbon moiety containing up to fourteen carbons, e.g., o-, m- and p-phenylene, and those substituted with one or two groups selected from $C_1$–$C_4$-alkyl, $C_1$–$C_4$-alkoxy or halogen.

In a preferred embodiment, the invention describes a process for the isolation and purification of phenyl ester salts. The phenyl ester salt to be isolated may be from a reaction product mixture with the reaction solvent (or a portion thereof) removed. Or, the starting phenyl ester salt may be the product after drying. Preferred dryers are mechanically agitated dryers capable of handling viscous material such as a Porcupine dryer from Bethlehem Corporation, Easton, Pa. or a List dryer from List Corporation, Acton, Mass. Alternatively, the starting phenyl ester salt may have been previously worked up to remove unwanted impurities, reaction by-products, solvent, color bodies, etc. The synthesis of phenyl ester salts which may be used as bleach activators, is discussed in U.S. Pat. No. 4,634,551, U.S. Pat. No. 4,852,989, U.S. Pat. No. 5,393,905, U.S. Pat. No. 5,523,434, U.S. Pat. No. 5,650,527, and WO 94/18159, which are hereby incorporated in their entirety.

In a particularly preferred embodiment, the invention relates to phenyl ester salts such as sodium 4-sulfophenyl-6-[(1-oxynonyl)amino] hexanoate, sodium 4-(nonanoyloxy) benzenesulfonate, or sodium benzoyloxy benzenesulphonate. However, this process may generally be used to isolate and purify chemical compounds and their salts, in addition to those described in detail below. The discussion below illustrates the invention in terms of this preferred embodiment.

When the process is used to purify a phenyl ester salt, the first step of the process comprises combining in any order: a first solvent, a second solvent, and a mixture comprising a phenyl ester salt, with at least one impurity. The mixture comprising the phenyl ester salt with at least one impurity may be any type of mixture. For example, the crude reaction mixture in which the phenyl ester salt is produced may be used. The mixture used in this invention may also be a crude solid or paste which is obtained by isolating the crude material through either filtration, centrifugation, or distillation. Alternatively, the mixture may have been produced from a prior purification of the compound. Accordingly, the invention is a general method for isolation and purification, and is applicable and easily adaptable to a broad class of mixtures.

The mixture of the phenyl ester salt with at least one impurity may be dissolved in a combination of the first and second solvents. Alternatively, the mixture may first be dissolved in one solvent, with subsequent addition of the second solvent prior to the end of the crystallizing step. Optionally, the solvents may be preheated prior to the step where they are combined with the mixture.

The solvents are selected such that the phenyl ester salt is substantially soluble in the first solvent and substantially insoluble in the second solvent. The impurity should be substantially soluble in the second solvent. Additionally, the second solvent is substantially immiscible in the first solvent under conditions where the phenyl ester salt crystallizes from the first solvent.

The first solvent should also be chosen such that the phenyl ester salt will dissolve at higher temperatures and crystallize at lower temperatures. For many phenyl ester salts the first solvent may be an aqueous solvent, water, or a polar organic solvent. However, other suitable solvents, as will be apparent to one skilled in the art, may also be used.

The second solvent should be substantially insoluble in the first solvent at the temperature at which the phenyl ester salt crystallizes from the first solvent. The phenyl ester salt should also be significantly insoluble in the second solvent. The second solvent should not react with the phenyl ester salt. Any impurities should partition to a greater extent in the second solvent than in the first solvent. The second solvent will preferably have some characteristic that makes it easy to recover from the primary liquid phase and the organic solid phase. The second solvent may be added either before or during the course of crystallization. In this invention, careful selection of the secondary solvent allows for improvement of the separability and purity of the phenyl ester salt without compromising on the yield.

Both the first and second solvents are normally low boiling to allow removal in the drying step once the desired product is obtained in the desired purity. Preferably, the process temperatures should not exceed the boiling point of the solvent system, or the equipment would have to be pressurized. The temperature should not drop below the freezing point of the solvent system, as the formation of a second solid phase would contaminate the solid phase of the desired product.

Suitable solvent systems include various combinations of water, methyl isobutyl ketone, cyclohexanol, ethyl acetate, 1-pentanol, methyl isopropyl ketone, hexane, xylene, and diethyl-ketone. Organic solvents of similar polarity and hydrogen bonding characteristics could also be employed as alternative solvents. Mixtures of solvents that approximate these polar and hydrogen bonding characteristics can also be employed.

The mixture comprising the phenyl ester salt with at least one impurity is substantially dissolved in at least one of the first and second solvents. The ratio of aqueous to organic solvent will depend upon the chemical compound being crystallized is not limited to particular values. However, in a preferred embodiment of the invention the ratio of the aqueous to organic solvent may vary from about 100:1 to 1:100, from about 30:1 to 1:30, or from about 5:1 to about 1:5. The solvents and mixture may optionally be agitated as required to substantially dissolve the mixture comprising the phenyl ester salt. It may also be necessary to heat the solvent or solvent system in order to dissolve the crude product. This is typically accomplished by heating to a temperature at which decomposition of the phenyl ester salt is minimized. A temperature range of about 50–100° C. is typically used.

Next, any undissolved material is optionally removed from the mixture resulting from the steps described above prior to the crystallizing step. This can be accomplished, for example by filtration or other methods known in the art.

Prior to the crystallization step, the pH of the aqueous layer may optionally be adjusted to within a range of from about 1 to about 6.9, a range from about 6.5 to about 4.5, or to about 5.5 with the use of an acid. Examples of commonly used acids include mineral acids, such as sulfuric acid, nitric acid, hydrochloric acid, and phosphoric acid, or organic acids. Typical organic acids include, but are not limited to, carboxylic acids, aliphatic acids such as benzoic acid and salicyclic acid, dicarboxylic acids (such as oxalic acid, malonic acid, succinic acid, glutaric acid, adipic acid, pimelic acid, maleic acid, fumaric acid, phthalic acid, and sebaic acid), fatty acids (including aliphatic fatty acids such as oleic acid, palmitic acid, and stenaric acid or aromatic fatty acids such as phenylstearic acid) and amino acids. The acid may be added in any suitable form including: fuming, concentrated or glacial forms of the acid, aqueous solutions, or anhydrides of the acid.

Prior to or during the crystallizing step, a second solvent phase forms which extracts the hydrophobic impurities out of the water phase and keeps them dissolved during the crystallization, thereby preventing co-crystallization of the impurities with the phenyl ester salt. The second phase is formed during some phase of the crystallization, however. For best results, the second phase should form early enough to avoid inclusion of impurities in the crystals. In a preferred embodiment, the second phase may be formed during the course of the cooling. In a preferred embodiment, crystallization is effected by cooling or evaporation, and it is not necessary to add the second solvent in order to induce crystallization. Alternatively, the second solvent may be added during the crystallization. Crystallization may occur in either the organic or aqueous phase, with impurities dissolved in the opposite phase.

The phenyl ester salt is crystallized from the first solvent under conditions where the impurity remains substantially dissolved in the second solvent. The crystallization step may be effected by methods known in the art. Typical means of forming crystals is either cooling or evaporation. For example, the crystallization step may optionally be carried out by cooling. The cooling step should be carried out to be consistent with good crystallization and good economics. A slower rate of cooling may provide better results, such as larger crystal size. Preferably, the rate of cooling is at a rate of about 8–15° C./hour. Crystallization may also be effected by evaporating a sufficient amount of the first solvent from the combined solvents and the mixture to induce crystallization of the salt of the phenyl ester salt. Since extraction and crystallization occur at the same time it may be desirable to agitate the solution during the crystallization step, as an optional step. The agitation in the equipment should be adequate to ensure good mass and heat transfer.

The collecting step is accomplished generally through methods known in the art, such as filtration or centrifugation. In particular, it has been found that a tricanter centrifuge is particularly useful for this purpose because it separates the three phase mixture into two separate liquid streams and one solids stream in one piece of equipment. However, other acceptable techniques known in the art may also be used, as will be apparent to one of ordinary skill in the art.

The impurities contained in the second phase may optionally be recovered and, if appropriate, recycled in a subsequent step. This may have economic advantages, particularly for a large-scale or commercial process. In some cases, the impurities are unreacted starting materials, and their subsequent and separate recovery may be desired.

This invention may be easily adapted to any scale. For large scale production, this process can be carried out in a variety of types of crystallizes that are listed in state-of-the-art reviews (e.g., Meyers, C. G., et al., "Crystallization Operation, Handbook of Separation Process Technology," R. W. Rousseau, Ed., 578–643, 1987; Mullin, J. W., "Ullmann's Encyclopedia of Industrial Chemistry," Volume B2, 3-1, 1988). Since extraction and crystallization occur at the same time, the agitation in the equipment should be adequate to ensure good mass and heat transfer, particularly for large scale reactions. This process can also be adapted to continuous, semibatch or batch modes.

For large scale applications, batch, semi-batch, and continuous crystallization may be appropriate. Batch crystallization processes add the solution to be crystallized to a vessel as a lot and then carrying out the crystallization process. Semibatch crystallization (sometimes referred to as semicontinuous) feeds or adds additional solution during crystallization or removal of the product crystals. A continuous crystallization utilizes a continuous feed of the solution to be crystallized and a continuous removal of the product crystals. While batch and semibatch processes are normally performed in a single vessel, continuous processes can require multiple agitated vessels in series. The larger the desired capacity of the process the more likely the process will be a continuous one since the operating cost of batch processes are normally much higher than continuous processes. However, there are times when the perhydrolysis rate of a phenyl ester salt can be more readily achieved in a batch process, but is not conveniently achieved in a continuous process. The semibatch process is a technique used to maximize output of a plant that would otherwise be batch.

Figure 1:
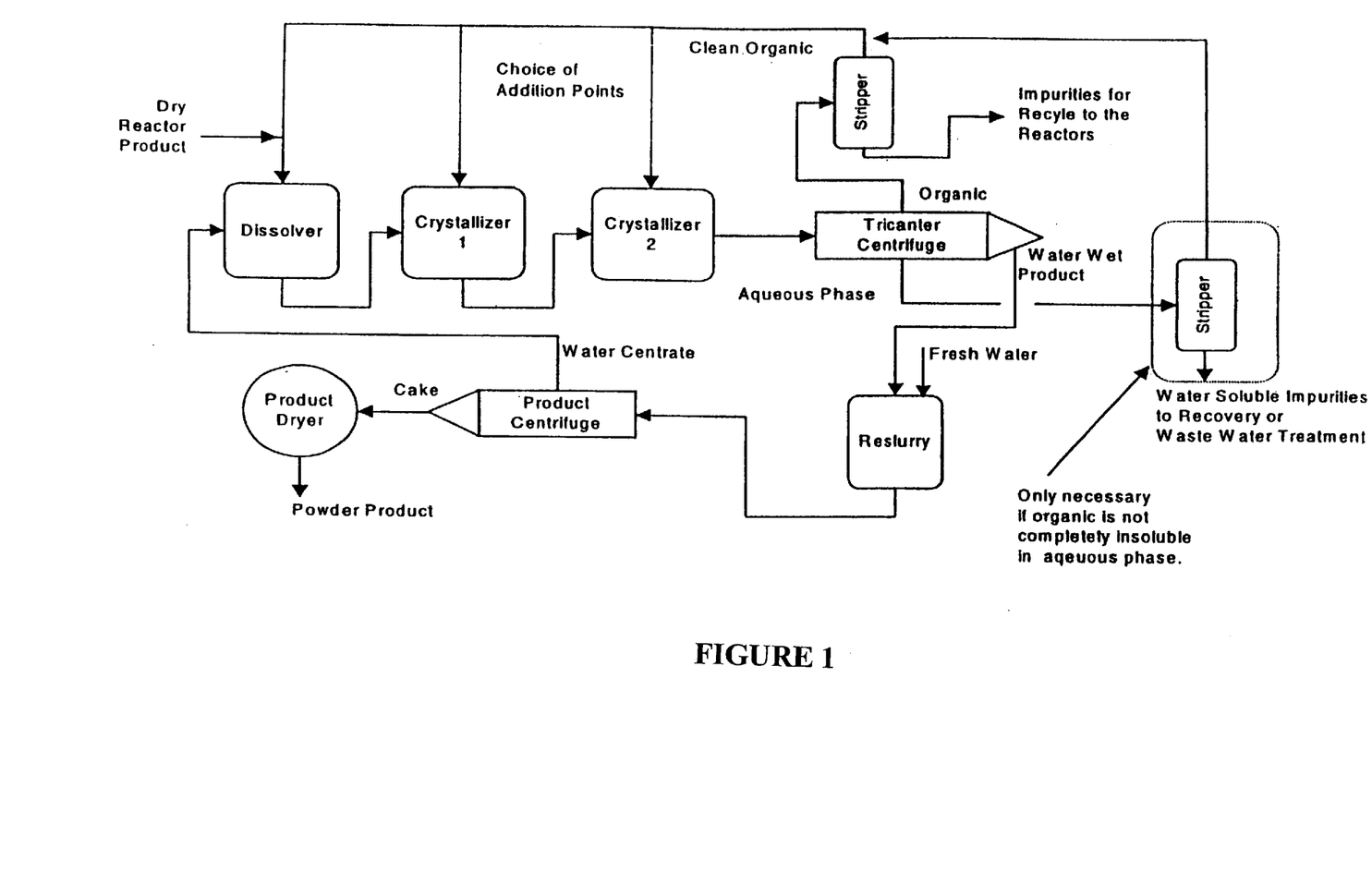
FIG. 1 illustrates the process of extractive solution crystallization, where the solution is crystallized in one or more continuous crystallizers where an organic extractant is added at the optimal time in the optimal amount.
Figure 2:
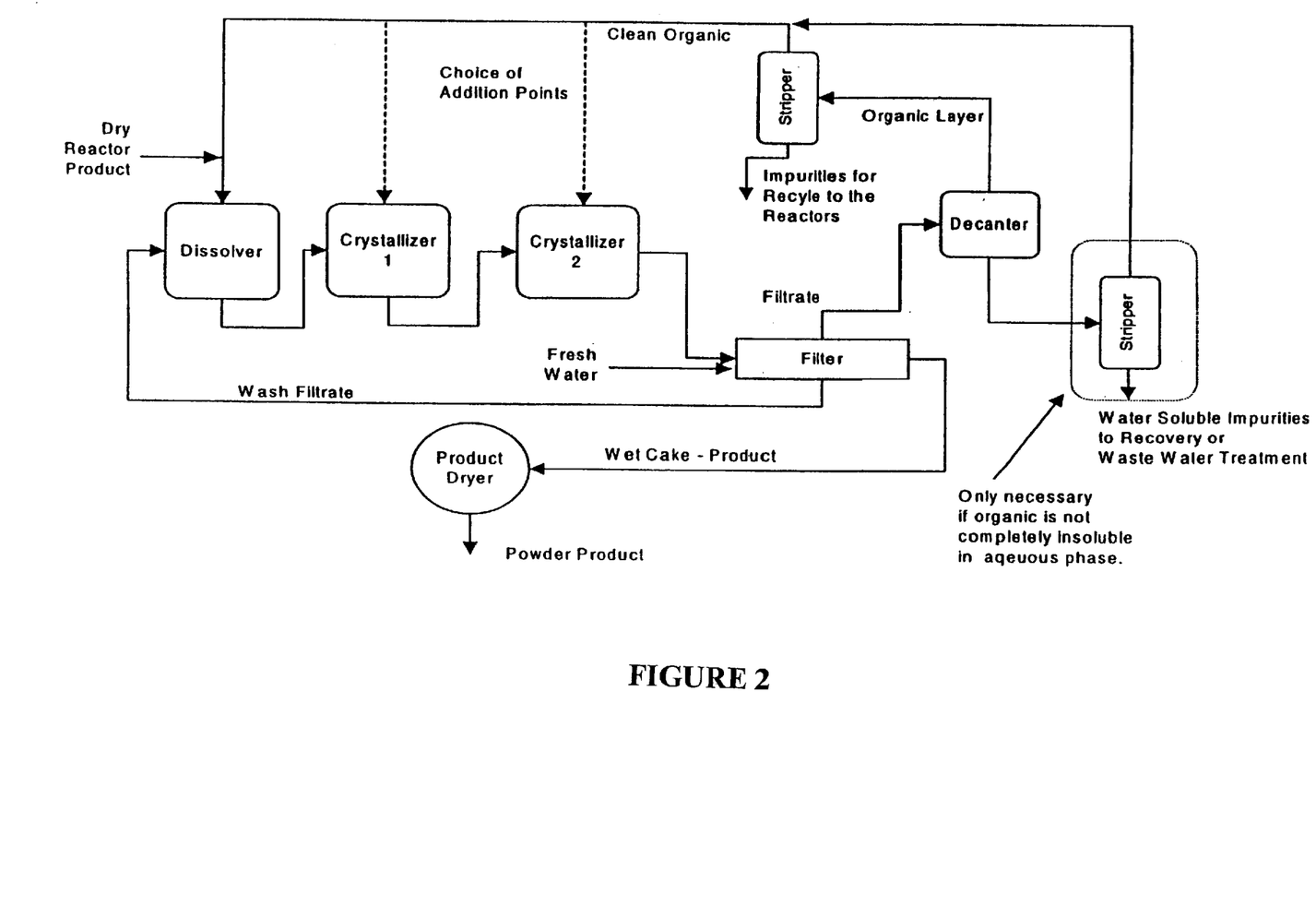
FIG. 2 illustrates the process of extractive solution crystallization, where the solution is crystallized in one or more continuous crystallizers where an organic extractant is added at the optimal time in the optimal amount, and where a separation device is used after the crystallizers that removes and washes the solid product.

FIGS. 1 and 2 illustrate the process of extractive solution crystallization. As shown in FIG. 1, Crude dry reactor product containing impurities is continuously charged to a dissolver along with recycled water from the product centrifuge. This solution is crystallized in one or more continuous crystallizers where an organic extractant is added at the optimal time in the optimal amount. The resulting slurry is separated into three phases; (1) a liquid organic phase containing the oil soluble impurities, (2) a water wet solid product containing the desired organic crystal, and (3) a liquid aqueous phase containing water soluble impurities and minimal amounts of dissolved product. The organic stream is sent to a stripper where the oil soluble impurities are remove and the extractant is purified for recycle. The Aqueous stream is sent to a separate striper where any dissolved organic extractant is recovered and the water stream with impurities is set to recovery of disposal. The product stream is re-slurried and centrifuged again as a wash step prior to drying.

The process shown in FIG. 2, is similar to that of FIG. 1. This example is similar to the first. The difference here is the use of separation device after the crystallizers that removes and washes the solid product but can not separate the aqueous phase from the liquid-organic phase. The two-phase liquid stream is then be decanted in a separate device prior to recovery of the organic and oil soluble impurities in a stripping device. The stripper on the lower aqueous phase is needed only if the extractant is not completely insoluble in the aqueous phase. The wet cake can be sent to the dryer for production of the final product.

In a particularly preferred embodiment, the invention relates to a process for the isolation and purification of phenyl ester salts such as sodium 4-sulfophenyl-6-[(1-oxynonyl)amino] hexanoate, sodium 4-(nonanoyloxy) benzenesulfonate, or sodium benzoyloxy benzenesulphonate.

In a further particularly preferred embodiment, the phenyl ester salt, sodium 4-sulfophenyl-6-[(1-oxynonyl)-amino] hexanoate, is purified by extractive solution crystallization. Sodium 4-sulfophenyl 6-[(1-oxynonyl)-amino] hexanoate is useful as a bleach activator (See e.g., U.S. Pat. No. 4,634,551; and U.S. Pat. No. 4,852,989) and can be synthesized through a variety of routes. One synthetic route involves the reaction of sodium 4-hydroxybenzenesulfonate, acetic anhydride, and nonanamidohexanoic acid in sulfolane with sodium acetate, imidazole, and/or caustic as catalysts(s).

Due to the cost of the sulfolane, the recovery of this solvent is required for good economics. One of the recovery methods for sulfolane is direct evaporation of the reaction mixture in which the phenyl ester salt is produced (e.g., U.S. Pat. No. 5,466,840). Through evaporation, the sulfolane is removed while the impurities remain with the sodium 4-sulfophenyl-6-[(1-oxynonyl)-amino] hexanoate. In this process, the impurities must then be removed by further purification, so the product meets desired specifications, such as color, rate of perhydrolysis or purity. For use in detergents and laundry formulations, there may be a variety of requirements, including a desired color and purity. In addition, the rate of perhydrolysis is a measure of the effectiveness of the bleach activator, and is the amount of phenyl ester salt that undergoes hydrolysis within a certain amount of time at a given temperature.

Thus, the invention provides a more efficient separation and purification of sodium 4-sulfophenyl-6-[(1-oxynonyl)-amino] hexanoate from water in a single step without pre-extracting water insoluble impurities or compromising on the yield, stability, or purity of the product. This invention alleviates problems encountered previously when crystallizing sodium 4-sulfophenyl-6-[(1-oxynonyl)-amino] hexanoate directly from water, including slow filtering and foaming during the filtration step.

A further aspect of this invention is that the impurities that are dissolved in the second solvent may easily be isolated and recycled. These impurities may include unreacted starting material, or other useful side products, for instance. For large-scale production, this may be a highly desirable advantage. For example, this is an advantage in a process for making sodium 4-sulfophenyl-6-[(1-oxynonyl)-amino] hexanoate from the reaction of sodium 4-hydroxy benzenesulfonate, acetic anhydride, and nonanamidohexanoic acid in sulfolane with sodium acetate, imidazole, and/or caustic as catalysts(s), as described in U.S. Pat. No.

5,650,527. This invention will allow for the recovery of excess nonanamidohexanoic acid from the second solvent, which means that an excess of nonanamidohexanoic acid starting material may be used in this reaction. Using an excess of nonanamidohexanoic acid starting material, reduces the amount of unreacted sodium 4-hydroxy benzenesulfonate (SPS), which is another starting material. Reducing the amount of unreacted SPS reduces waste of this reagent which previously was unrecovered, and also reduces the load on the waste water treatment facilities.

While the invention is described in detail for phenyl ester salts, it should be noted that this invention should not be restricted to crystallization from the aqueous phase. There may be situations where it is possible to effect crystallization from the organic phase, while the undesired impurities remain dissolved in the aqueous phase to prevent co-crystallization. Moreover, this invention describes a process that may be used in the isolation and purification of a broad class of salts of chemical compounds.

BRIEF DESCRIPTION OF THE EXAMPLES

The crude phenyl ester salt used in these examples is sodium 4-sulfophenyl-6-[(1-oxynonyl)-amino] hexanoate which has been prepared from the reaction of sodium 4-hydroxy benzenesulfonate, acetic anhydride, and nonanamidohexanoic acid in sulfolane with sodium acetate, imidazole, and/or caustic as catalysts(s), as described in U.S. Pat. No. 5,650,527 which is incorporated herein in its entirety.

The cake moisture was determined by gravimetric analysis (i.e., weight loss upon drying). Powder color was measured using a Hunterlab Colorquest II spectrophotometer. The samples are analyzed as dry powders in reflectance mode, using a standard powder cell. Standard reflectance tiles are used prior to each analysis to calibrate the spectrophotometer to ensure consistency and accuracy. For commercial use as a bleach activator, a Hunter L value of 85 or greater and Hunter a and b values near zero are generally desired. The particle size was measured by a Malvern Autosizer using light scattering of dilute suspensions. The final compound purity was determined by using liquid chromatography.

EXAMPLES

Example 1

A jacketed 1.5-liter crystallizer with 3 baffles, 1 thermocouple, and a 2" high-efficiency impeller was charged with 400 grams of demineralized water and heated to 75° C. Once the water reached the desired temperature, 100 grams of crude reaction mixture containing sodium 4-sulfophenyl-6-[(1-oxynonyl)-amino] hexanoate, (where the reaction solvent had been removed by distillation), was charged to the vessel and mixed to form a solution. The crude sodium 4-sulfophenyl 6-[(1-oxynonyl)-amino] hexanoate assay is given in Table 1. Agitation was set at 600 rpm. The solution was held for thirty minutes at 75° C. to allow the sodium 4-sulfophenyl 6-[(1-oxynonyl)-amino] hexanoate to dissolve. The solution was then cooled to 30° C. at 15° C./hr, and held at 30° C. for one hour. The phenyl ester salt crystallized out of solution forming a slurry.

A 250-gram aliquot of this slurry was filtered on a coarse-fritted glass filter (79 mm ID) that was preheated to 30° C. Filtrate collection proceeded very slowly. After 16 minutes on the filter with 19"Hg vacuum, only 30 mLs of filtrate was collected. The filtration was stopped without a firm cake being formed. The resulting filtrate was analyzed, and the results are shown in Table 1. Loss of the phenyl ester salt to the filtrate was only 1.1%. The crystals had a median size of 45 micron.

Example 1 demonstrates the poor performance of sodium 4-sulfophenyl-6-[(1-oxynonyl)-amino] hexanoate crystallization with only water at a low temperature. Although the yield is satisfactory, the nonanamidohexanoic acid and di-nonanamido hexanoic acid have come out of solution and sufficiently slowed the filtration process down, such that it is not economically viable. Several filters of maximum size would be required for the plant capacity needed. However, the slow filtering nature of the cake also results in a cake that has high levels of impurities.

Example 2

The slurry remaining from Example 1 was heated to 40° C. and held at this temperature for 30 minutes. This slurry (containing about 180 grams of the phenyl ester salt) was filtered at room temperature on a coarse-fritted glass filter with 19"Hg vacuum. The filtration proceeded much quicker. About 125 g of filtrate was collected in less than one minute. The wet cake was removed and weighed 55 grams. Analyses of the cake and filtrate are shown in Table 1. The median particle size was determined to be 35 microns. The yield from this filtration was estimated at 91%. The analytical data show higher than expected levels of nonanamidohexanoic acid and SPS. This is likely due to hydrolysis of sodium 4-sulfophenyl 6-[(1-oxynonyl)-amino] hexanoate while in water at the elevated temperatures.

Example 2 demonstrates the poor performance of sodium 4-sulfophenyl-6-[(1-oxynonyl)-amino] hexanoate crystallization when carrying out the filtration step at a temperature of 40° C. with only water. Although the rate of filtration is acceptable for commercial use, there is a higher level of impurities formed at the higher temperature due to hydrolysis of the phenyl ester salt at elevated temperatures, and an unacceptable amount of sodium 4-sulfophenyl-6-[(1-oxynonyl)-amino] hexanoate is lost to the filtrate due to its greater solubility at higher temperatures.

Example 3

A jacketed 1-liter model reactor with one 2.25" A310 agitator and four baffles was assembled. Demineralized water (620 grams) was added to the vessel and heated to 80° C. About 180 grams of poor quality crude sodium 4-sulfophenyl 6-[(1-oxynonyl)-amino] hexanoate (analysis in Table 1) was charged to the vessel and dissolved. The Hunter color of the crude material was L=71.0, a=1.05, and b=5.56. The solution (about 14 wt % sodium 4-sulfophenyl 6-[(1-oxynonyl)-amino] hexanoate) was held at 80° C. for 60 minutes and then cooled to 20° C. at 8° C./hour. Once at ambient conditions, 34 grams of cyclohexanol was added to the slurry and the mixture was held for a minimum of 60 minutes. Two portions of approximately 250 grams of slurry were removed from the vessel and filtered at 20"Hg vacuum on a coarse-fritted glass filter.

The first cake, Example 3A, was washed with 5% cyclohexanol solution in water. The second cake, Example 3B, was washed with 95% cyclohexanol in water. For Example 3A, the time to collect 132 grams of filtrate was 127 seconds, and the where the filtrate contained 2.6% sodium 4-sulfophenyl 6-[(1-oxynonyl)-amino] hexanoate and 9.6% cyclohexanol. The cake contained 42% moisture. The purity of the final dried product was 86% as measured by HPLC (high pressure liquid chromatography). All impurities were reported at levels less than 0.25%. The Hunter color of the dried powder was L=88.5, a=0.16, and b=1.78. For Example 3B, the final dried cake was analyzed to be 89.5% sodium 4-sulfophenyl 6-[(1-oxynonyl)-amino] hexanoate with all impurities reported at less than 0.2%. The Hunter color results were L=87.8, a=0.22, and b=2.15.

Example 3 demonstrates that the second solvent should be added prior to the end of the crystallization process, and the second liquid phase should form early enough to prevent contamination of the desired crystals with co-crystallized impurities or inclusions of mother liquor containing the impurities.

In contrast to examples 1–2, examples 3–6 provide extractive solution crystallization processes whereby the co-solvent extracts out the nonanamidohexanoic acid selectively over the sodium 4-sulfophenyl 6-[(1-oxynonyl)-amino] hexanoate to allow easy separation of the phenyl ester salt. Tables 1 and 2 summarize these results.

TABLE 1

LC Analysis for Examples 1–3 (all results given in estimated wt. %)

| Sample | I | II | III | IV | V | VI | VII |
|---|---|---|---|---|---|---|---|
| Example 1&2 Crude | 81.5 | 0.72 | 5.80 | 4.17 | 1.27 | 1.31 | 0.13 |
| Example 1&2 Crystallization Slurry | 16.3 | 0.14 | 1.16 | 0.83 | 0.25 | 0.26 | 0.03 |
| Example 1 Filtrate | 1.13 | 0.17 | 0.35 | 0.92 | 0.39 | 0.46 | 0.06 |
| Example 2 Filtrate | 2.14 | 0.17 | 1.17 | 0.97 | 0.41 | 0.44 | 0.04 |
| Example 2 Cake | 46.9 | 0.44 | 1.23 | 0.61 | 0.27 | 0.27 | — |
| Example 3 Crude | 70.1 | 7.3 | 2.4 | 3.9 | 0.6 | 2.8 | 8.0 |
| Example 3 Cake | 86.2 | 0.21 | 0.05 | 0.04 | — | 0.04 | 0.08 |

I. sodium 4-sulfophenyl 6-[(1-oxynonyl)-amino] hexanoate
II. sodium 4-(nonanoyloxy) benzenesulfonate
III. di-sodium 4-sulfophenyl 6-[(1-oxynonyl)-amino] hexanoate
IV. di-nonanamidohexanoic acid
V. nonanamidohexanoic acid
VI. 4-hydroxy benzenesulfonate
VII. sodium acetyloxybenzene sulfonate Example 4

A jacketed 1-liter model reactor with one 2.25" A310 agitator and four baffles was set up. A charge of 500 grams of water and 300 grams of methyl-isobutyl-ketone (MIBK) was added to the vessel and heated to 75° C. An amount of 200 grams of crude sodium 4-sulfophenyl 6-[(1-oxynonyl)-amino] hexanoate was charged to the vessel and dissolved. The crude assay was reported as 89.4% sodium 4-sulfophenyl 6-[(1-oxynonyl)-amino] hexanoate, 1.14% nonanamidohexanoic acid, 3.76% di-nonanamidohexanoic acid, 1.9% sodium 4-(nonanoyloxy) benzenesulfonate, and 1.8% di-sodium 4-sulfophenyl 6-[(1-oxynonyl)-amino] hexanoate with a Hunter color of L=76, a=1.1, and b=6.7. The agitation speed was set at 500 rpm. The pH of the solution was adjusted with $H_2SO_4$ to 5.5 and the solution was held at 75° C. for 60 minutes and then cooled to 22° C. at 8° C./hour. An aliquot of 236 grams was removed from the vessel and filtered with 20" Hg vacuum on a coarse-fritted glass filter. The cake was washed twice in place, once with 2% MIBK in water and then by 99% MIBK in water. The filtration time to collect 71 grams of filtrate was 191 seconds; the filtrate was two-phase and the composite analyzed to be 2.3% sodium 4-sulfophenyl 6-[(1-oxynonyl)-amino] hexanoate. The upper (organic) phase was analyzed to be 89% MIBK, 1.98% nonanamidohexanoic acid, 0.22% di-nonanamidohexanoic acid, and only 0.04% sodium 4-sulfophenyl 6-[(1-oxynonyl)-amino] hexanoate. After drying, the purity of the final product was 96.2% with a measured Hunter color of L=89, a=0.1, and b=2.7. The cake moisture was determined to be 50%. The median particle size was reported to be 131.9 microns.

Example 4 shows an improvement in purity and color compared to Example 3.

Example 5

A portion (197 g) of the slurry remaining from Example 4 was centrifuged at 2500 G's for 5 minutes. The filtrate (87.3 g) was decanted and the cake was mixed with 60 grams of water to form a slurry. The centrifugation was repeated, followed by a decant. This reslurry/centrifuge/decant procedure was repeated twice more with 69 and 74 grams of fresh water. The final cake (75.6 g) had 64.8% moisture and upon drying assayed to be 98.1% sodium 4-sulfophenyl 6-[(1-oxynonyl)-amino] hexanoate with all impurities reported to be less than 0.5%. The Hunter colored was determined to be L=89, a=0.07, and b=2.3, while the median particle size was measured as 134.5 microns.

Example 5 shows an improvement in purity and color compared to Example 3.

Example 6

Figure 3:
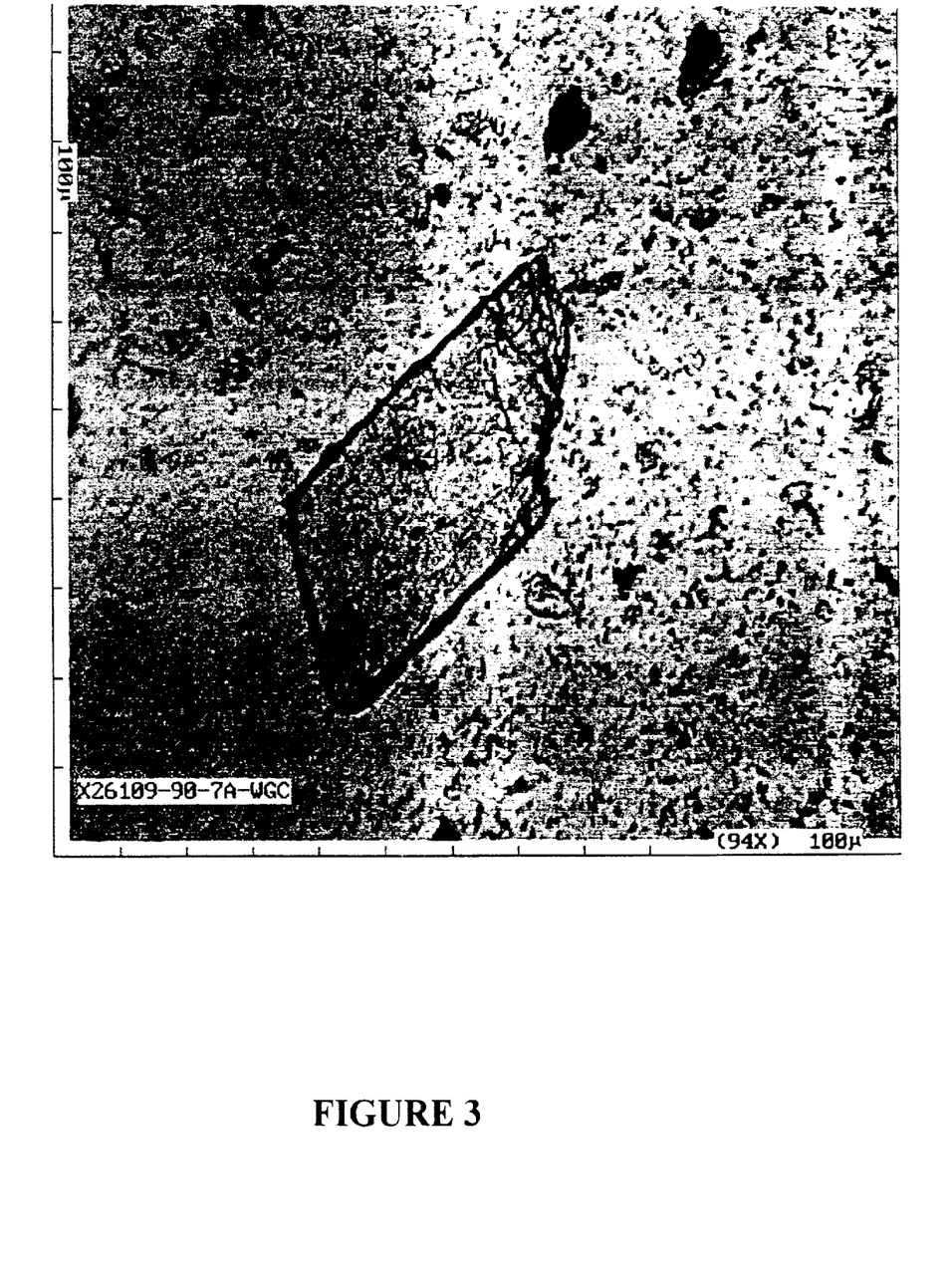
FIG. 3 illustrates the shape of a sodium 4-sulfophenyl-6-[(1-oxynonyl)-amino] hexanoate crystal after purification by extractive solution crystallization; the crystal appears as a perfect rectangular platelet with a median size of 264 microns.

A jacketed 1-liter model reactor with 4 baffles and 1–2.25" A310 agitator was utilized. A charge of 60 grams of water and 540 grams of MIBK was added to the vessel and the mixture was heated to 85° C. A charge of 200 grams of the crude material used in Example 4 was charged to the vessel and dissolved. The agitation speed was set at 320 rpm. The pH of the solution was adjusted to 5.5 with $H_2SO_4$ and the solution was held a 75° C. for 60 minutes and then cooled to 22° C. at 8° C./hour. An aliquot of 167 grams of slurry was removed from the vessel and centrifuged for 15 minutes at 2500 G's. The centrate appeared to be two phases and was decanted (95 grams). After addition of 60 grams of water, the cake was mixed to form a slurry and the mixture was centrifuged again. This step was repeated twice more with 60 grams of water each time. The final wet cake was analyzed for assay, particle size, and color. The purity of the final product was greater than 99% on a dry basis, with a measured Hunter color of L=89.4, a=0.03, and b=2.1. The crystals appeared as perfect rectangular platelets with a median size of 264 microns, which is much larger than observed in all the previous examples; see FIG. 3.

Example 6 shows the improvement over Examples 1–5. This result is due to adjusting the proportions of the first solvent and the second solvent.

TABLE 2

Extractive Solution Crystallization (Examples 1–6)

| Example | #1 | #2 | #3A | #3B | #4 | #5 | #6 |
|---|---|---|---|---|---|---|---|
| I. Amount of first solvent | 400 g water | 400 g water | 620 g water | 620 g water | 500 g water | 500 g water | 60 g water |
| Amount of second solvent | — | — | — | 300 g MIBK | 300 g MIBK | 500 g MIBK |
| Heated to a temp. of: | 75° C. | 75° C. | 80° C. | 80° C. | 75° C. | 75° C. | 85° C. |
| II. Amount of mixture containing phenyl ester salt | 100 g | 100 g | 180 g | 180 g | 200 g | 200 g | 200 g |
| Initial hunter color of mixture containing phenyl ester salt: | | | L = 71.0 a = 1.05 b = 5.56 | L = 71.0 a = 1.05 b = 5.56 | L = 76 a = 1.1 b = 6.7 | L = 76 a = 1.1 b = 6.7 | L = 76 a = 1.1 b = 6.7 |
| Agitation (rpm) | 600 rpm | 600 rpm | | | 500 rpm | 500 rpm | 320 rpm |
| pH of first solvent adjusted to: | — | — | | | 5.5 with $H_2SO_4$ | 5.5 with $H_2SO_4$ | 5.5 with $H_2SO_4$ |
| held at a temperature of: | 75° C. | 75° C. | 80° C. | 80° C. | 75° C. | 75° C. | 75° C. |
| for time of: | 30 min | 30 min | 60 min | 60 min | 60 min | 60 min | 60 min |
| III. cooled to a temperature of: | 30° C. | 40° C. | 20° C. | 20° C. | 22° C. | 22° C. | 22° C. |
| at rate of: | 15° C./hr | | 8° C./hr | 8° C./hr | 8° C./hr | 8° C./hr | 8° C./hr |
| added second solvent: | — | | 34 g cyclo-hexanol | 34 g cyclo-hexanol | | | |
| held at a temperature of: | 30° C. | 40° C. | | | | | |
| for time of: | 60 min. | 30 min. | ≧60 min. | ≧60 min. | | | |
| IV. Amount filtered | 250 g | 180 g | 250 g | 250 g | 236 g | | |
| Amount of filtrate collected | 30 mL | 125 g | 132 g | | 71 g | | |
| In a time of: | 16 min/stopped | <60 sec | 127 sec | — | 191 sec | | |
| Wash solvent composition (% second Solvent in first solvent) | | | 5% | 95% | first wash: 2%, second wash: 99% | | |
| Amt centrifuged: | | | | | | 197 g | 167 g |
| for time of: | | | | | | 5 min. | 15 min. |
| at centrifugal force of: | | | | | | 2500 g | 2500 g |
| V. final cake moisture | | | 42% | 50% | 64.8% | | |
| final hunter color of phenyl ester salt: | | | L = 88.5 a = 0.16 b = 1.78 | L = 87.8 a = 0.22 b = 2.15 | L = 89 a = 0.1 b = 2.7 | | L = 89.4 a = 0.03 b = 2.1 |
| final purity: | | | 86% | | 96.2% | 98.1% | >99% |
| Particle size: | 45 micron | 35 microns | | | 131.9 microns | 134.5 microns | 264 microns |

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference in their entirety.

The claimed invention is:

1. A process for the purification and isolation of a phenyl ester salt by extractive solution crystallization, comprising the steps of:

(i) combining in any order: a first solvent, a second solvent, and a crude phenyl ester salt with at least one impurity, wherein the phenyl ester salt is substantially soluble in the first solvent and substantially insoluble in the second solvent and the impurity is substantially soluble in the second solvent, and wherein the second solvent is substantially immiscible in the first solvent under conditions where the phenyl ester salt crystallizes from the first solvent;

(ii) substantially dissolving the crude phenyl ester salt in the combined solvents;

(iii) optionally, removing any remaining undissolved material from steps (i) or (ii);

(iv) crystallizing the phenyl ester salt from the first solvent under conditions where the impurity remains substantially dissolved in the second solvent; and (v) collecting the crystals.

2. A process of claim 1, wherein the first solvent is an aqueous solvent, water, or polar organic solvent.

3. A process of claim 2, wherein the second solvent is at least one of cyclohexanol, methyl isobutyl ketone, ethyl acetate, 1-pentanol, methyl isopropyl ketone, hexane, xylene, or diethylketone.

4. A process of claim 1, further comprising, prior to the combining step (i), the step of preheating at least one of the first solvent or second solvent to a temperature ranging from about 50° C. to about 100° C.

5. A process of claim 1, further comprising, after the combining step (i), the step of heating the first solvent, the second solvent, and the mixture combined in step (i) to a temperature ranging from about 50° C. to about 100° C.

6. A process of claim 2, wherein the first solvent is an aqueous solvent or water, and further comprising, prior to the crystallizing step (iv), the step of adjusting the pH of the first solvent to a pH of about 4–6.

7. A process of claim 6, wherein the pH is adjusted by adding a mineral acid.

8. A process of claim 7, wherein the mineral acid is sulphuric acid.

9. A process of claim 1, wherein the crystallizing step (iv) comprises cooling the combined solvents and the mixture to a temperature sufficient to crystallize the phenyl ester salt from the first solvent.

10. A process of claim 9, wherein the crystallizing step (iv) comprises cooling at a rate of about 8–15° C./hour.

11. A process of claim 1, wherein the crystallizing step (iv) comprises evaporating a sufficient amount of the first solvent from the combined solvents and the mixture to induce crystallization of the phenyl ester salt without evaporating a substantial amount of the second solvent, thereby avoiding crystallization of the impurity.

12. A process of claim 1, wherein the collecting step (v), comprises filtering or centrifuging the combined solvents and the mixture after the crystallizing step (iv).

13. A process of claim 12, wherein the collecting step (v) comprises using a tricanter centrifuge.

14. A process of claim 1, wherein the phenyl ester salt is a compound of formulae (I) or (II):

(I)

(II)

wherein $R^1$ is selected from $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl;

$R^2$ and $R^5$ are each independently selected from hydrogen, $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl, or in formula II, $R^2$ and $R^5$, together with the nitrogen carrying them, form a $C_3$–$C_{10}$ heterocycle;

$R^3$ and $R^4$ are each independently selected in each instance from hydrogen, $C_1$–$C_{10}$ alkyl, $C_2$–$C_{10}$ alkenyl, $C_2$–$C_{10}$ alkynyl, $C_3$–$C_{10}$ cycloalkyl, and $C_6$–$C_{10}$ aryl, or $R^3$ and $R^4$, together with the carbon carrying them, form a $C_3$–$C_{10}$ cycloalkyl;

Y is selected from $SO_3^-M^+$, $CO_2^-M^+$, $SO_4^-M^+$, and $N^+(R^6)_3X^-$;

M is selected from hydrogen, ammonium and alkali metal atom;

$R^6$ in each instance is a $C_1$–$C_4$ alkyl group;

X is a halide, hydroxide, methylsulfate, or acetate ion;

m is an integer from 0 to 1; and n is an integer from 0 to 20.

15. A process of claim 14, wherein the phenyl ester salt is a compound of formulae (I) or (II), wherein $R^1$ is selected from $C_6$–$C_{10}$ alkyl, and $C_6$–$C_{10}$ aryl;

$R^2$ is hydrogen;

$R^3$ in each instance is independently selected from hydrogen and methyl;

$R^4$ in each instance is independently selected from hydrogen and methyl;

$R^5$ is selected from hydrogen, $C_6$–$C_{10}$ alkyl, and $C_6$–$C_{10}$ aryl;

Y is selected from $SO_3^-M^+$, and $CO_2^-M^+$;

M is a sodium ion;

m is an integer from 0 to 1; and n is an integer from 0 to 6.

16. A process of claim 15, wherein the phenyl ester salt is sodium 4-sulfophenyl-6-[(1-oxynonyl)-amino] hexanoate, sodium 4-(nonanoyloxy) benzenesulfonate, or sodium benzoyloxy benzenesulphonate.

17. A process for the purification and isolation of a chemical compound by extractive solution crystallization, comprising the steps of:

(i) combining in any order: a first solvent, a second solvent, and a mixture comprising a chemical compound and at least one impurity, wherein the chemical compound is substantially soluble in the first solvent and substantially insoluble in the second solvent and the impurity is substantially soluble in the second solvent, and wherein the second solvent is substantially immiscible in the first solvent under conditions where the chemical compound crystallizes from the first solvent;

(ii) substantially dissolving the mixture in the combined solvents;

(iii) optionally, removing any remaining undissolved material from steps (i) or (ii);

(iv) crystallizing the chemical compound from the first solvent under conditions where the impurity remains substantially dissolved in the second solvent; and (v) collecting the crystals.

18. A process of claim 17, wherein the first solvent is an aqueous solvent, water, or polar organic solvent.

19. A process of claim 17, further comprising, prior to the combining step (i), the step of preheating at least one of the first solvent or second solvent to a temperature ranging from about 50° C. to about 100° C.

20. A process of claim 17, further comprising, after the combining step (i), the step of heating the first solvent, the second solvent, and the mixture combined in step (i) to a temperature ranging from about 50° C. to about 100° C.

21. A process of claim 18, wherein the first solvent is an aqueous solvent or water, and further comprising, prior to the crystallizing step (iv), the step of adjusting the pH of the first solvent to a pH of about 4–6.

22. A process of claim 17, wherein the crystallizing step (iv), comprises cooling the combined solvents and the mixture to a temperature sufficient to crystallize the phenyl ester salt from the first solvent.

23. A process of claim 22, wherein the crystallizing step (iv), comprises cooling at a rate of about 8–15° C./hour.

24. A process of claim 17, wherein the crystallizing step (iv), comprises evaporating a sufficient amount of the first solvent from the combined solvents and the mixture to induce crystallization of the phenyl ester salt without evaporating a substantial amount of the second solvent, thereby avoiding crystallization of the impurity.

25. A process of claim 17, wherein in the chemical compound is a salt of an organic compound or a salt of an inorganic compound.

* * * * *